United States Patent [19]

Zimmerman et al.

[11] Patent Number: 5,279,305

[45] Date of Patent: Jan. 18, 1994

[54] ELECTROENCEPHALOGRAPH INCORPORATING AT LEAST ONE WIRELESS LINK

[75] Inventors: Andrew W. Zimmerman; Brian T. Pepper; David V. Blankenship, all of Knox, Tenn.

[73] Assignee: Pedifutures, Inc., Oak Ridge, Tenn.

[21] Appl. No.: 926,230

[22] Filed: Aug. 6, 1992

[51] Int. Cl.⁵ .......................................... A61B 5/0476
[52] U.S. Cl. ................................... 128/731; 128/903
[58] Field of Search ............... 128/639, 640, 644, 731, 128/732, 903, 904

[56] References Cited

U.S. PATENT DOCUMENTS

| | | | |
|---|---|---|---|
| 3,253,588 | 5/1966 | Vuilleumier et al. | 128/2 |
| 3,807,387 | 4/1974 | MacNichol, Jr. | 128/731 |
| 3,859,988 | 1/1975 | Lencioni, Jr. | 128/2.1 B |
| 3,943,918 | 3/1976 | Lewis | 128/2.1 A |
| 4,089,329 | 5/1978 | Couvillon, Jr. et al. | 128/2 T |
| 4,186,749 | 2/1980 | Fryer | 128/748 |
| 4,204,546 | 5/1980 | Smith et al. | 128/731 |
| 4,245,645 | 1/1981 | Arsenault et al. | 128/642 |
| 4,279,258 | 7/1981 | John | 128/731 |
| 4,409,987 | 10/1983 | McIntyre | 128/731 |
| 4,471,786 | 9/1984 | Inagaki et al. | 128/748 |
| 4,495,950 | 1/1985 | Schneider | 128/670 |
| 4,681,111 | 7/1987 | Silvian | 128/903 |
| 4,800,888 | 1/1989 | Itil et al. | 128/644 |
| 4,862,359 | 8/1989 | Trivedi et al. | 128/731 |

Primary Examiner—William E. Kamm
Assistant Examiner—George Manuel
Attorney, Agent, or Firm—Pitts & Brittian

[57] ABSTRACT

An improved EEG system (10) for telemetrically transmitting brain activity data from a portable transmitter to a processing console. The improved EEG system (10) includes a lightweight transmitter (12) which amplifies and digitizes the EEG signals from a set of electrodes (16) and transmits the digital signals along with a checksum to a receiver (14). The transmitter (12) may be carried by the subject under observation. The transmitter (12) of the preferred embodiment includes at least four circuit boards including a selectively interchangeable montage board (18), an amplifier board (24), a processor board (34), and a transmitter board (54). A signal is transmitted toward the receiver (14) and delivered to a conventional computer-controlled broadcast television tuner (80). The selected receiver (14) outputs data which is in an acceptable form for connection to standard microprocessor peripherals. The incoming data is processed and inspected to verify the validity thereof with any invalid data being marked as invalid. All data is then continuously and simultaneously displayed and recorded, with any invalid data being easily recognized as such and therefore disregarded.

14 Claims, 8 Drawing Sheets

ELECTROENCEPHALOGRAPH INCORPORATING AT LEAST ONE WIRELESS LINK

TECHNICAL FIELD

This invention relates to the field of monitoring brain activity. More specifically, this invention relates to an electroencephalograph (or EEG) device for monitoring and recording brain activity wherein wireless links are incorporated for communication between activity-detecting electrodes and a processing device.

BACKGROUND ART

In the field of monitoring brain activity the use of electroencephalograph devices (EEG's) is well known. EEG's are used to measure and record small electrical signals which occur on the surface of the scalp as a result of brain activity. Typically, an EEG system includes a plurality of electrodes attached at selected positions on the subject's scalp, a corresponding number of lead wires, and a processing console. Typically, each electrode is connected to the processing console via a separate lead wire. The processing console is provided for signal selection, amplification, and conditioning. Also included in EEG systems are means for measuring electrode impedance, calibrating equipment, and observing and permanently recording data processed by the processing console.

It is well known that the processing console and the observation and recording equipment are often incorporated within a single unit. The single unit, however, is too large to be easily transportable by the subject under observation. Further, because long wires between the electrodes and the processing console are impractical, the subject must remain relatively stationary when using most available EEG systems.

Some EEG systems have been developed to overcome the problem of the subject having to remain still during observation. These devices include portable recorders which may be carried by the subject under observation. These systems do not, however, include means for contemporaneous observation of the record. It is well known that such observation is often desired.

One method for making EEG measurements and contemporaneous observations more practical is to replace the wire links between the electrodes and the processing console with wireless links. Thus, situations such as those described above—i.e., when long wires might encumber other simultaneous attention needed by the subject or when the mobility of the subject might be impaired—would be at least partially resolved.

Other devices have been produced to monitor, process and record data received from the vital organs of a body. Typical of the art are those described in the following U.S. Patents:

| U.S. Pat. No. | Inventor | Issue Date |
| --- | --- | --- |
| 3,253,588 | R. F. Vuilleumier, et al. | May 31, 1966 |
| 3,859,988 | C. C. Lencioni, Jr. | Jan. 14, 1975 |
| 3,943,918 | R. A. Lewis | Mar. 16, 1976 |
| 4,089,329 | L. A. Couvillon, Jr., et al. | May 16, 1978 |
| 4,186,749 | T. B. Fryer | Feb. 5, 1980 |
| 4,245,645 | P. M. Arseneault, et al | Jan. 20, 1981 |
| 4,279,258 | E. R. John | Jul. 21, 1981 |
| 4,409,987 | R. A. McIntyre | Oct. 18, 1983 |
| 4,471,786 | H. Inagaki, et al. | Sep. 18, 1984 |
| 4,495,950 | D. E. Schneider | Jan. 29, 1985 |

Of these patents, the U.S. Pat. Nos. 3,253,588 ('588); 3,943,918 ('918); 4,089,329 ('329); 4,186,749 ('749); and 4,471,786 ('786) patents disclose devices which incorporate telemetric transmittal of sensed data to a selected processing center. Each discloses a device using transmission over radio frequencies (r-f) using amplitude modulation (AM) or frequency modulation (FM) methods similar to those used for broadcast radio. The transmitted signals are thus subject to the same interference and distortion as broadcast radio signals.

It is well known that FM transmissions are more reliable than AM transmissions. However, it is also known that FM signals are subject to distortion and interference from signals broadcast from other stations. Though in the field of radio broadcasting these disturbances are mostly annoyances to signal receptors, in the field of EEG monitoring such disturbances will provide erroneous data concerning the brain activity of the subject. In this context, distortion and interference is detrimental to accurate analysis and is therefore undesirable.

Therefore, it is an object of this invention to provide a means for transmitting signals detected by electrodes placed on a subject's body to a signal processor using telemetric methods.

It is also an object of the present invention to substantially reduce the distortion and interference typically present in standard transmission of radio frequency signals.

Another object of the present invention is to provide an electroencephalographic monitoring and recording device wherein digital data communications is incorporated to provide accurate transmission of detected brain activity signals.

Still another object of the present invention is to provide a lightweight transmitter for amplifying and digitizing EEG signals from the electrodes.

Yet another object of the present invention is to provide a means whereby the data transmitted may be checked and verified to insure that data received by a receiving device is valid, and further that any invalid data received is ignored.

DISCLOSURE OF THE INVENTION

Other objects and advantages will be accomplished by the present invention which serves to detect brain activity in a subject and transmit the detected signals telemetrically to a processing center. The telemetric method used incorporates digital data communications in order to provide accurate transmittal of the detected signals. The improved EEG system of the present invention includes a lightweight transmitter which amplifies and digitizes the EEG signals from a set of electrodes and transmits the digital signals along with a checksum to a receiver. The checksum allows the receiver to verify the validity of the received data and to denote any data which has been distorted or subjected to interference between the transmitter and receiver.

The transmitter is designed to be carried by the subject under observation. A plurality of electrodes are electrically connected to the transmitter and are attached to the subject in a conventional fashion. The transmitter of the illustrated embodiment includes four circuit boards upon which the electronic circuitry is configured. These circuit boards include a selectively interchangeable montage board, an amplifier board, a processor board, and a transmitter board.

The montage board is provided for selectively configuring the connections between the electrodes and the remainder of the EEG system. The montage board may be selectively interchanged to change the configuration of the electrode connections.

The amplifier board is provided for amplifying the small signals detected by the electrodes. In the preferred embodiment, the amplifier board includes a plurality of signal amplifiers. The connection of the amplifiers to the electrodes is determined by the selected montage board installed with a selected pair of electrodes being connected to the respected inputs of a signal amplifier.

The processor board digitizes the amplified signals and converts them to a form suitable for transmission. The processor board includes a plurality of inputs for receiving the individual outputs of the signal amplifiers. In the preferred embodiment, the processor board is programmed to control multiplexing, conversion of the selected amplifier outputs within the A-D converter to binary-coded digital data, calculation of a binary checksum number, conversion of the binary-coded digital numbers and checksum number to a selected code suitable for transmission of digital data, and generation of a precisely-timed serial data stream from the numbers coded in the selected code.

The transmitter board further converts the signals into radio frequency (r-f) signals for transmission. The serial data stream generated by the microprocessor is delivered through an amplifier to an oscillator carried by the transmitter board. The amplifier is also used to select the rate of frequency change of the oscillator in order to conform to regulations imposed by the Federal Communications Commission (FCC) and further to meet other selected output requirements as well. The oscillator is also controlled by a phase-locked-loop system which will allow for the control of the center frequency of the oscillator.

The output of the oscillator is connected to an antenna via a trap, the trap serving to filter out unwanted harmonic frequencies in order to avoid interference with other transmissions.

The signal from the transmitter is received by the receiver antenna and delivered to a conventional computer-controlled broadcast television tuner. The output of the TV tuner is connected to a selected receiver. The combination of the TV tuner and the selected receiver form a double-superheterodyne receiver capable of rejecting out-of-band image signals.

The selected receiver outputs a reconstituted serial data stream substantially identical to the selectively-coded serial data stream generated by a microcontroller incorporated by the transmitter processor board. The data stream is sent to a decoder for converting the coded data stream to a synchronous nonreturn-to-zero code (NRZ) serial data stream. The synchronous NRZ serial data is an acceptable form for connection to standard microprocessor peripherals.

The incoming data is processed by a selected microprocessor which inspects the checksum generated by the transmitter microcontroller. For any checksum detected to be incorrect, the associated data is marked such that observation of the distorted data will reflect the distortion and can be easily disregarded. All data, whether valid or invalid, is sent to a second communications interface configured to perform as a standard asynchronous serial port which may be connected to any standard computer serial port. The data may then be displayed and recorded as desired.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

An electroencephalograph (EEG) system incorporating various features of the present invention is illustrated generally at 10 in the figures. The EEG system 10 is designed for adapting digital data communications techniques to the requirements of EEG recording. In the preferred embodiment the EEG system 10 includes a lightweight transmitter 12 which amplifies and digitizes the EEG signals from a plurality of electrodes 16 and transmits the digital signals along with a checksum to a selected receiver 14. The checksum allows the receiver 14 to verify the validity of the received data and to denote any data which has been distorted or subjected to interference between the transmitter 12 and receiver 14. It is envisioned, though not shown, that the lightweight transmitter 12 may also be used to transmitted EEG signals over standard telephone wire to a processing station at a remote location where telemetric signals may not be accurately transmitted.

Figure 1:
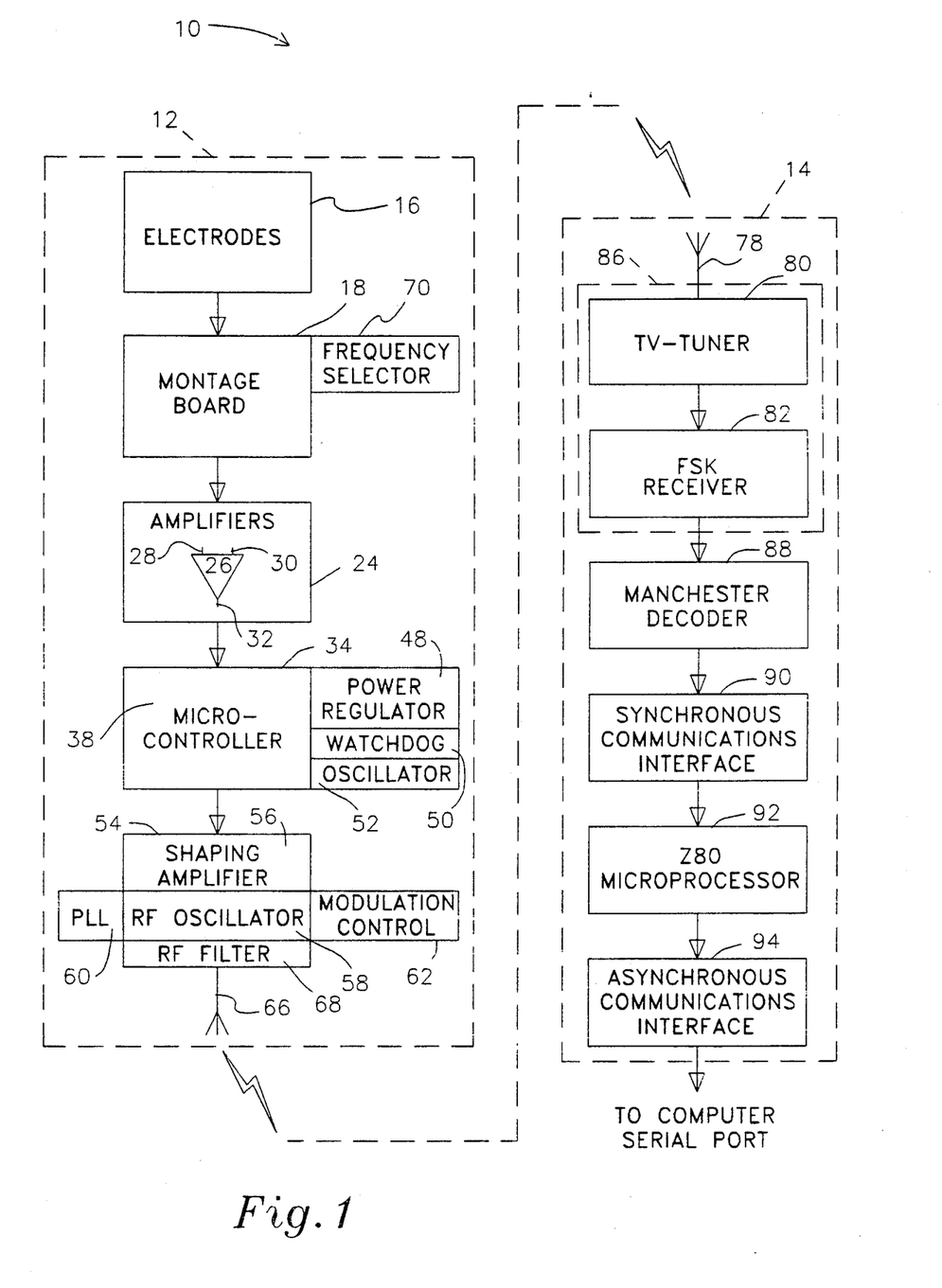
FIG. 1 is a block diagram illustrating the functions of a transmitter and a receiver constructed in accordance with several features of the present invention.

The transmitter 12 is designed to be carried by the subject under observation. A plurality of electrodes 16 is electrically connected to the transmitter 12 and is attached to the subject in a conventional fashion. The transmitter 12 of the illustrated embodiment includes four circuit boards upon which the electronic circuitry is configured. It is envisioned that the transmitter 12 may be constructed on any selected number of circuit boards. FIG. 1 illustrates the relationship between the four circuit boards.

Figure 2:
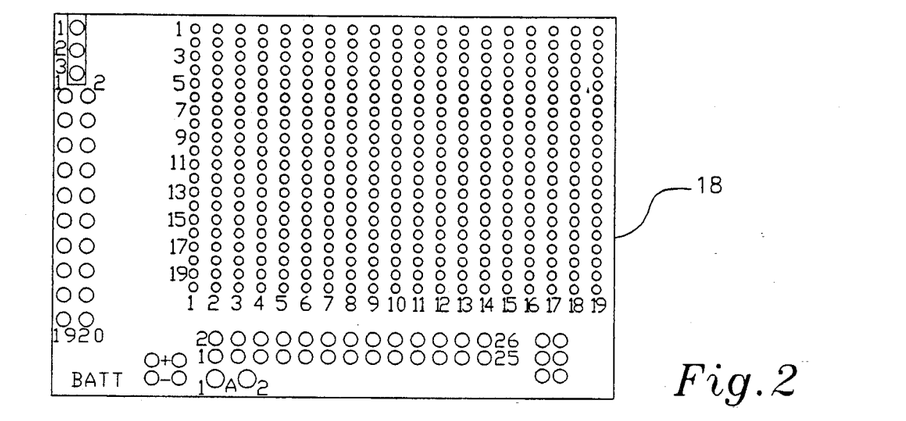
FIG. 2 is a plan view of a montage board incorporated within a transmitter of FIG. 1.
Figure 2A:
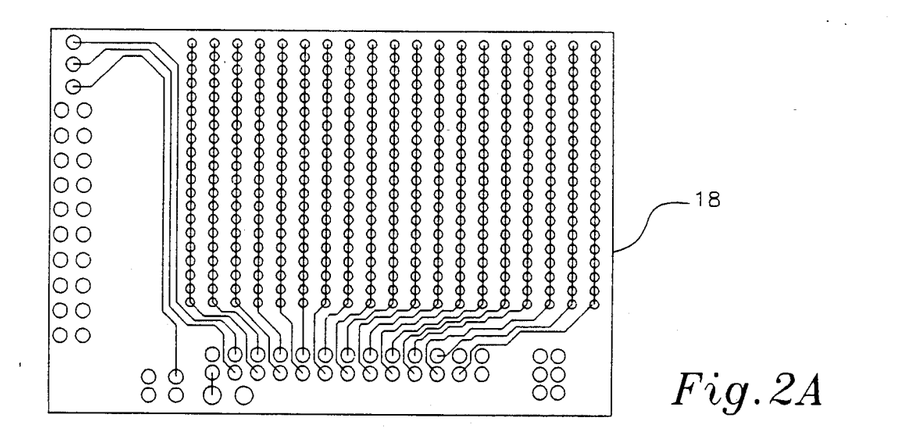
FIG. 2A is a plan view of the montage board of FIG. 2 showing a preferred etching schematic on a first side thereof.
Figure 2B:
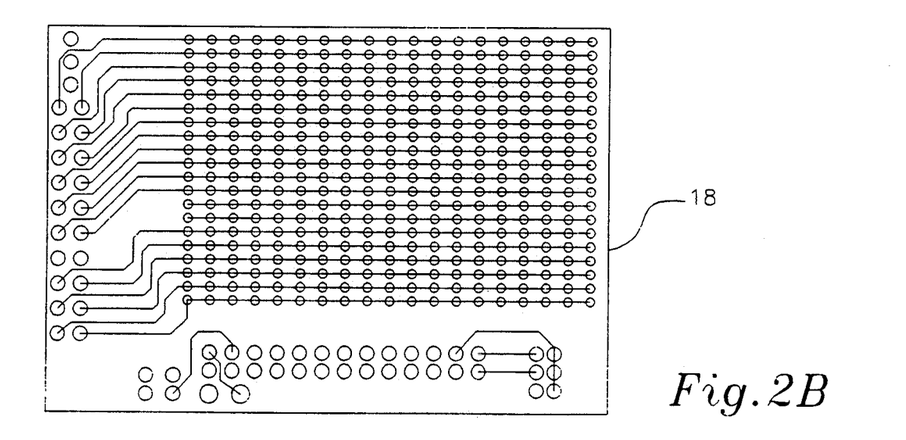
FIG. 2B is a plan view of the montage board of FIG. 2 showing a preferred etching schematic on a second side thereof.

A montage board 18 is provided for selectively configuring the connections between the electrodes 16 and the remainder of the EEG system 10. The operator of the EEG system 10 may alter the configuration of the electrode connections by replacing the montage board 18 with another defining the selected configuration. The electrodes 16 are connected to the montage board 18 in a conventional fashion as with a ribbon-type cable and connector. A typical montage board 18 is illustrated in FIGS. 2, 2A, and 2B.

Figure 3:
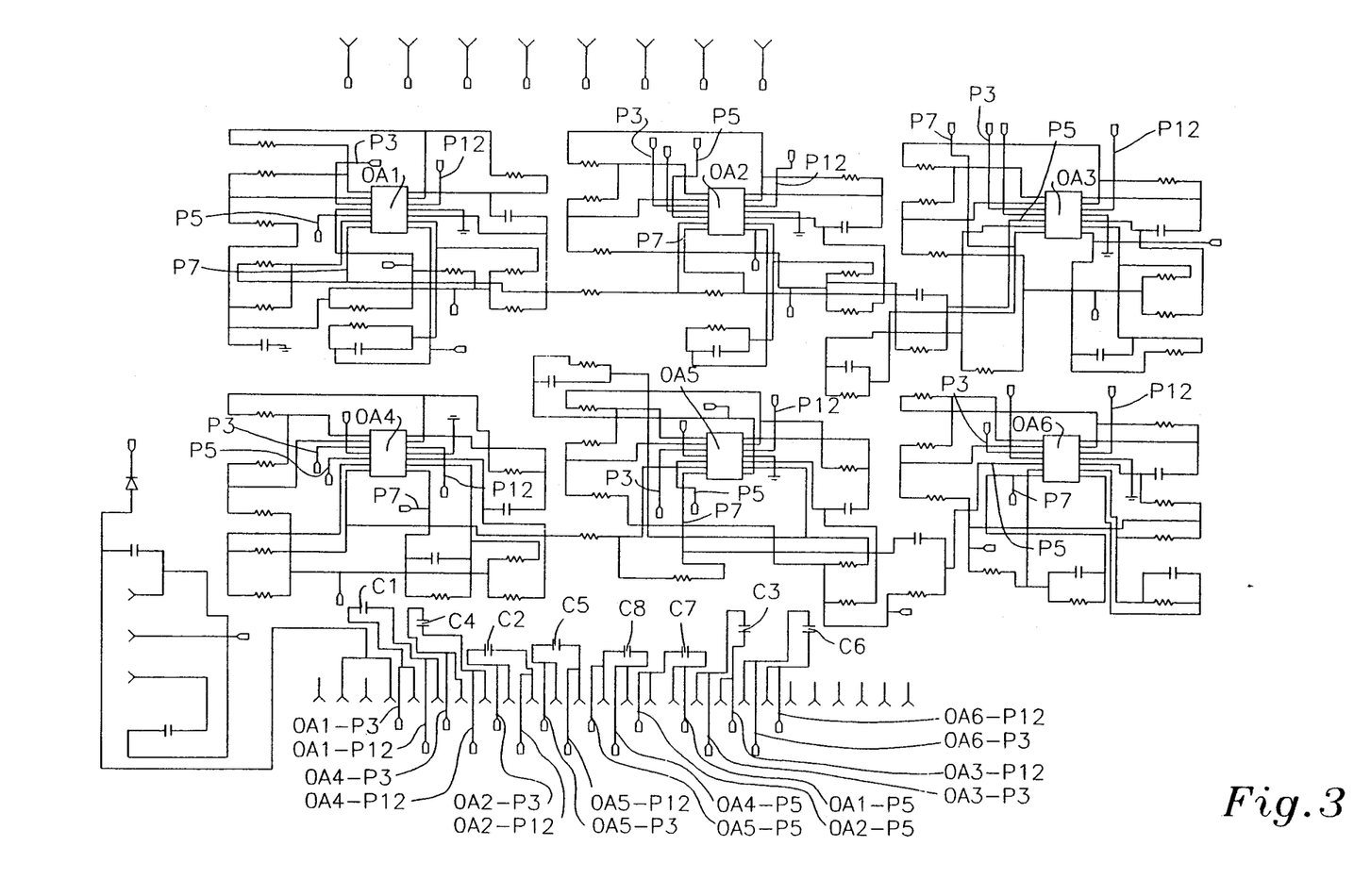
FIG. 3 is a schematic diagram of the circuitry of the amplifier board incorporated in the transmitter of FIG. 1.

An amplifier board 24 is provided for amplifying the small signals detected by the electrodes 18. In the preferred embodiment, the amplifier board 24 includes at least eight signal amplifiers illustrated generally at 26. The connection of the signal amplifiers 26 to the electrodes 16 is determined by the selected montage board 18 installed. A selected pair of electrodes 16 is connected to the respective inputs 28,30 of a signal amplifier 26.

Each of the signal amplifiers 26 uses three operational amplifier (op-amp) elements as opposed to the typical minimum of four. As shown in FIG. 3, six op-amps OA1-6 are included on the preferred amplifier board 24. Each op-amp OA1-6 shown includes four elements, or pins, which are designated for use in the signal amplifiers 26. These pins are designated as P3, P5, P7, and P12 for each op-amp OA1-6. The pins P3 and P12 of each op-amp OA1-6 are shown as being used as input pins while pin P7 of each op-amp OA1-6 is shown as being an output pin for the respective input pins P3 and P12. Thus, the respective sets of pins P3, P7, and P12 each define a single signal amplifier 26. The inputs OA1-P3 and OA1-P12, as illustrated, are connected in series with a selected capacitor C1 therebetween. The designation OA1-P3 denotes pin P3 of op-amp OA1, etc. The respective pairs of input pins from the op-amps OA2 through OA6 as described are configured in similar fashion with capacitors C2 through C6, respectively.

The pins P5 of the op-amps OA1 and OA2 are shown as inputs and pin P5 of the op-amp OA3 is shown as the output of a seventh signal amplifier 26. The pins P5 of the op-amps OA4, OA5, and OA6 are arranged in similar fashion to define an eighth signal amplifier 26. Inputs OA1-P5 and OA2-P5 are connected by a capacitor C7 while inputs OA4-P5 and OA5-P5 are connected by a capacitor C8.

It will be seen that one fewer op-amp is required for every four signal amplifiers 26 desired as described in the present invention. By utilizing fewer op-amps and other components, the requirements of high input-resistance in a differential input configuration and high gain are achieved These requirements are similar to those of a conventional EEG system.

Figure 4:
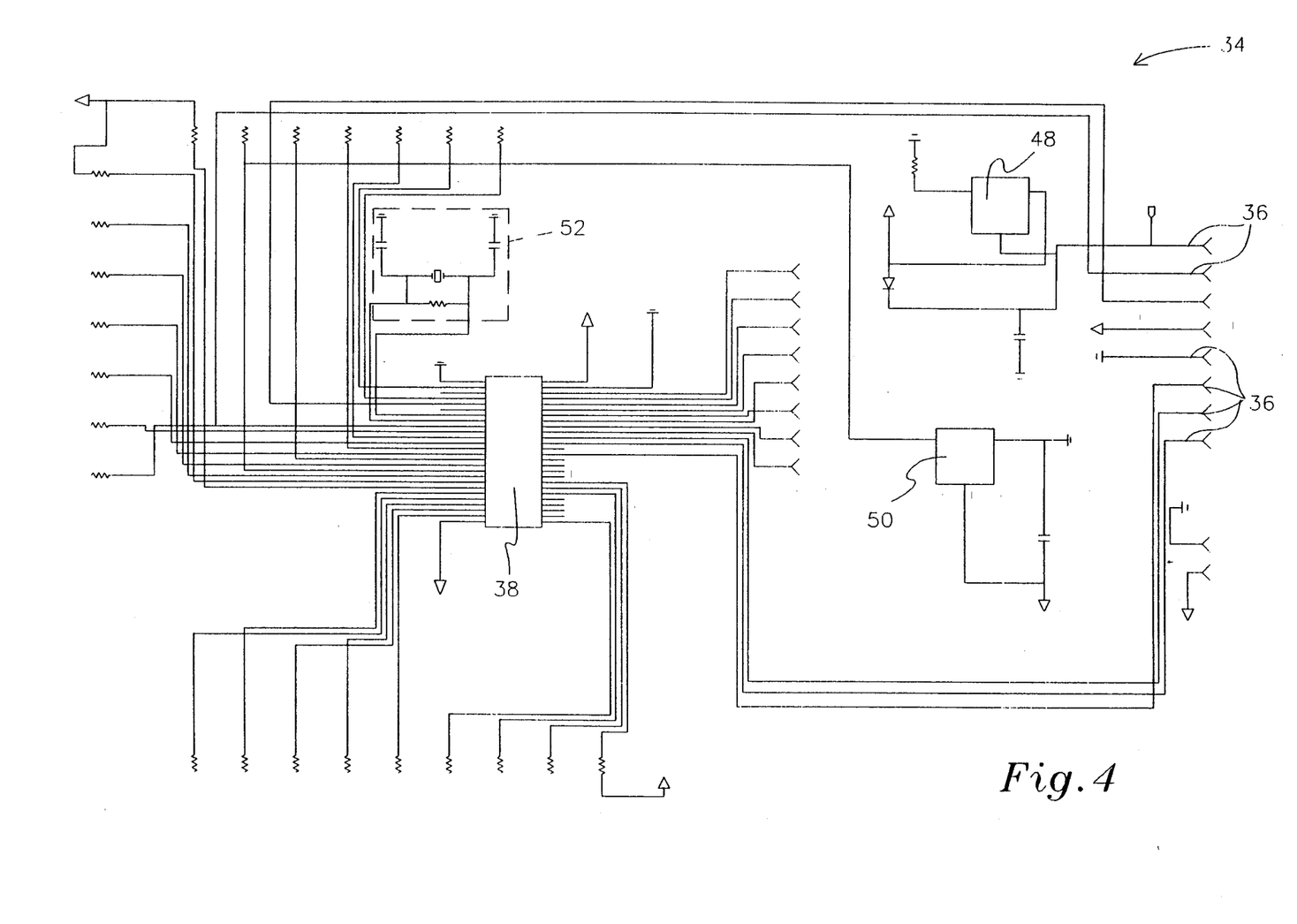
FIG. 4 is a schematic diagram of the circuitry of the processing board incorporated in the transmitter of FIG. 1.
Figure 5:
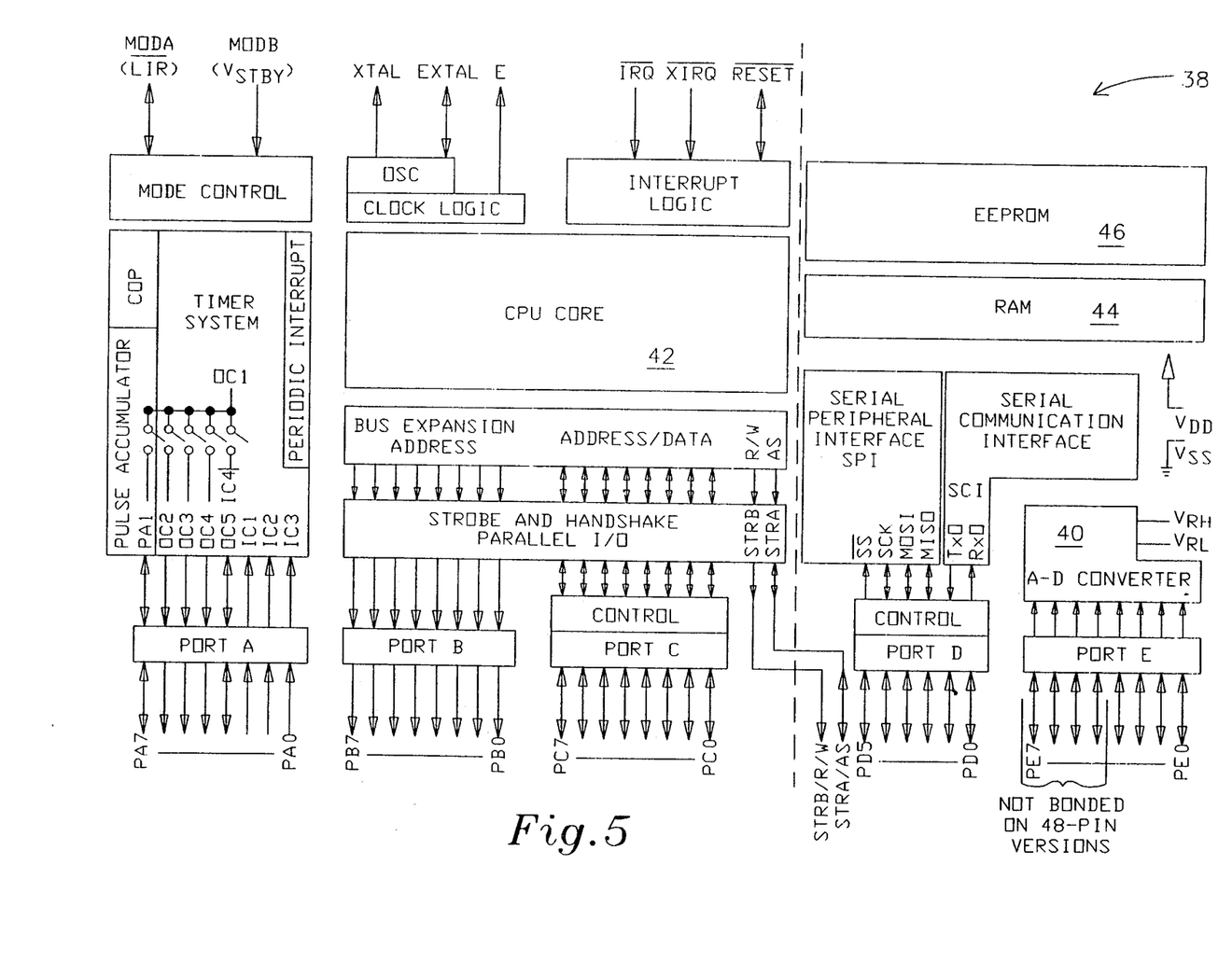
FIG. 5 is a schematic diagram of the circuitry of a preferred microcontroller incorporated in the processing board of FIG. 4.

A processor board 34 digitizes the amplified signals and converts them to a form suitable for transmission. The processor board 34 includes a plurality of inputs 36 for receiving the individual outputs 32 of the amplifiers 26. A microcontroller 38 is utilized in the preferred embodiment for combining the functions of an analog multiplexer and analog to digital (A-D) converter 40, a microprocessor 42, data memory 44, and non-volatile program memory 46. FIG. 5 illustrates, in block-diagram form, the functions of a preferred microcontroller 38. One microcontroller 38 which may be used is the MC68HC811E2 high-density CMOS (HCMOS) Microcontroller Unit (MCU) manufactured by Motorola.

The selected microcontroller 38 may be programmed to perform selected functions. In the preferred embodiment, the microcontroller 38 is programmed to control multiplexing, conversion of the selected amplifier outputs 32 within the A-D converter 40 to binary-coded digital data, calculation of a binary checksum number, conversion of the binary-coded digital numbers and checksum number to a selected code suitable for transmission of digital data, and generation of a precisely-timed serial data stream from the numbers coded in the selected code. One selected code which is preferred is known as the Manchester code, which will be discussed in more detail below.

The A-D converter 40 incorporated within the microcontroller 38 is capable of performing the first two processes. Namely, the A-D converter 40 performs the sequential selection of the signal amplifier outputs 32 for connection thereto, or multiplexing, and the conversion of the selected signal amplifier outputs 32 to binary-coded digital data. The digital data is temporarily stored in memory, such as in random access memory indicated at 44.

The microprocessor 42 performs the latter three functions. Specifically, the microprocessor 42 calculates a binary checksum number, converts the binary-coded digital numbers and checksum number to a selected code suitable for transmission of digital data, and generates a precisely-timed serial data stream from the numbers coded in the selected code. The A-D converter 40 is also controlled by the microprocessor 42. A voltage regulator 48, a watchdog 50, and the components of a crystal oscillator 52 are shown as typical peripherals to the microprocessor 42.

Figure 6:
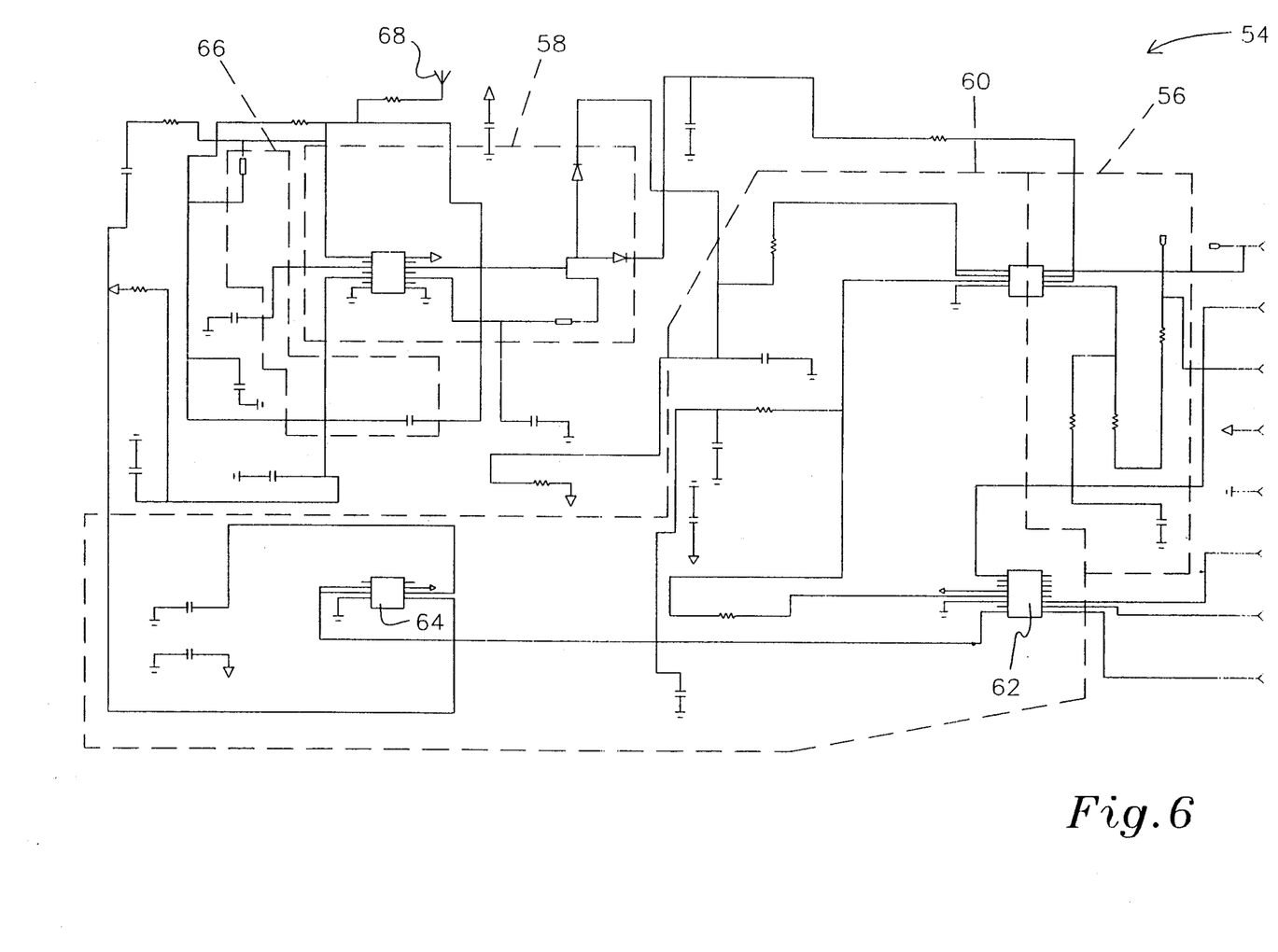
FIG. 6 is a schematic diagram of the circuitry of the transmitter board incorporated in the transmitter of FIG. 1.

A transmitter board 54 further converts the signals into radio frequency (r-f) signals for transmission. The serial data stream generated by the microprocessor 42 is delivered through an amplifier 56 to an oscillator 58 carried by the transmitter board 54. The amplifier 56 is also used to select the rate of frequency change of the oscillator 58 in order to conform to regulations imposed by the Federal Communications Commission (FCC). It will be noted that the rate of frequency change of the oscillator 58 may be selectively changed within the imposed regulations to meet other selected output requirements as well. The modulation of the oscillator 58 by a digital signal in this manner is typically denoted as frequency shift keying, or FSK.

The oscillator 58 of the illustrated embodiment is also controlled by a phase-locked-loop system 60 comprising at least two selected components 62,64. In the preferred embodiment, components 62,64 such as the MC145157, which is a serial input phase-locked-loop frequency synthesizer, and MC12023, which is a frequency divider, manufactured by Motorola may be used. The phase-locked-loop system 60 allows the center frequency of the oscillator 58 to be precisely controlled to conform to regulations imposed by the FCC and to be selectable by the microcontroller 38 incorporated in the processor board described above. The component 62 may select from at least two frequencies for the center frequency of the oscillator 58. The frequency is selected by the component 62 by monitoring a user-selectable input 70 carried by the montage board 18.

In the preferred embodiment, the response time of the control exerted on the oscillator 58 by the phase-locked-loop system 60 is longer than the response time of the control exerted by the FSK modulation input. The longer response time is desirable to prevent the negation of the effect of the FSK modulation control.

The output of the oscillator 58 is connected to an antenna 66 via a trap 68. The trap 68 serves to filter out unwanted harmonic frequencies in order to avoid interference with other transmissions.

The Manchester code referred to above has as its principal feature a substantially equal time spent in the two possible modulating states. Therefore, there is substantially little danger of a repeated coded sequence causing a bias to one state or the other when averaged over a period approaching the response time of the phase-locked-loop system 60. The use of binary code has been found to allow such biasing, which causes a shift of the center of the frequency of the oscillator 58. When such a frequency shift occurs, the performance of the overall system 10 may be impaired and FCC regulations may be contravened.

Figure 7:
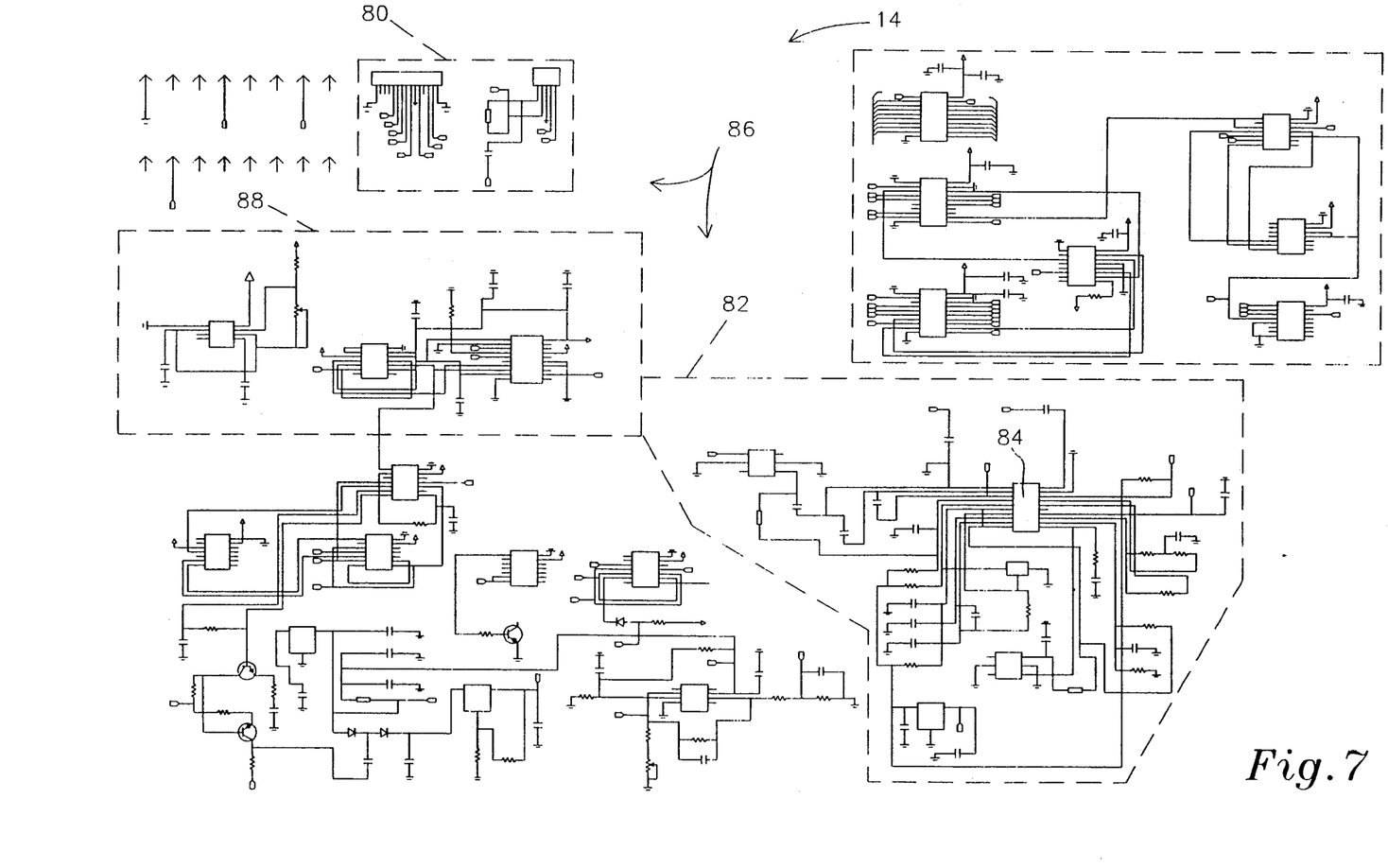
FIG. 7 is a schematic diagram of the circuitry of the receiver board incorporated in the receiver of FIG. 1.

Referring again to FIG. 1, the signal from the transmitter 12 is received by the receiver antenna 78 and delivered to a conventional computer-controlled broadcast television tuner 80. The output of the TV tuner 80 is connected to an FSK receiver 82 which includes at least one FSK receiver chip 84. One preferred FSK receiver chip 84 is the MC3356 manufactured by Motorola. The combination of the TV tuner 80 and the FSK receiver 82 form a double-superheterodyne receiver 86 capable of rejecting out-of-band image signals.

The FSK receiver 82 outputs a reconstituted serial data stream substantially identical to the selectively-coded serial data stream generated by the microcontroller 38 incorporated by the transmitter processor board 34. As described above, this serial data stream may be Manchester-coded in a preferred embodiment. The data stream is sent to a decoder 88 for converting the coded data stream to a synchronous nonreturn-to-zero code (NRZ) serial data stream. The synchronous NRZ serial data is an acceptable form for connection to a standard microprocessor peripheral 90. Typical of the standard microprocessor peripherals is the Intel 8251A communications interface.

Figure 8:
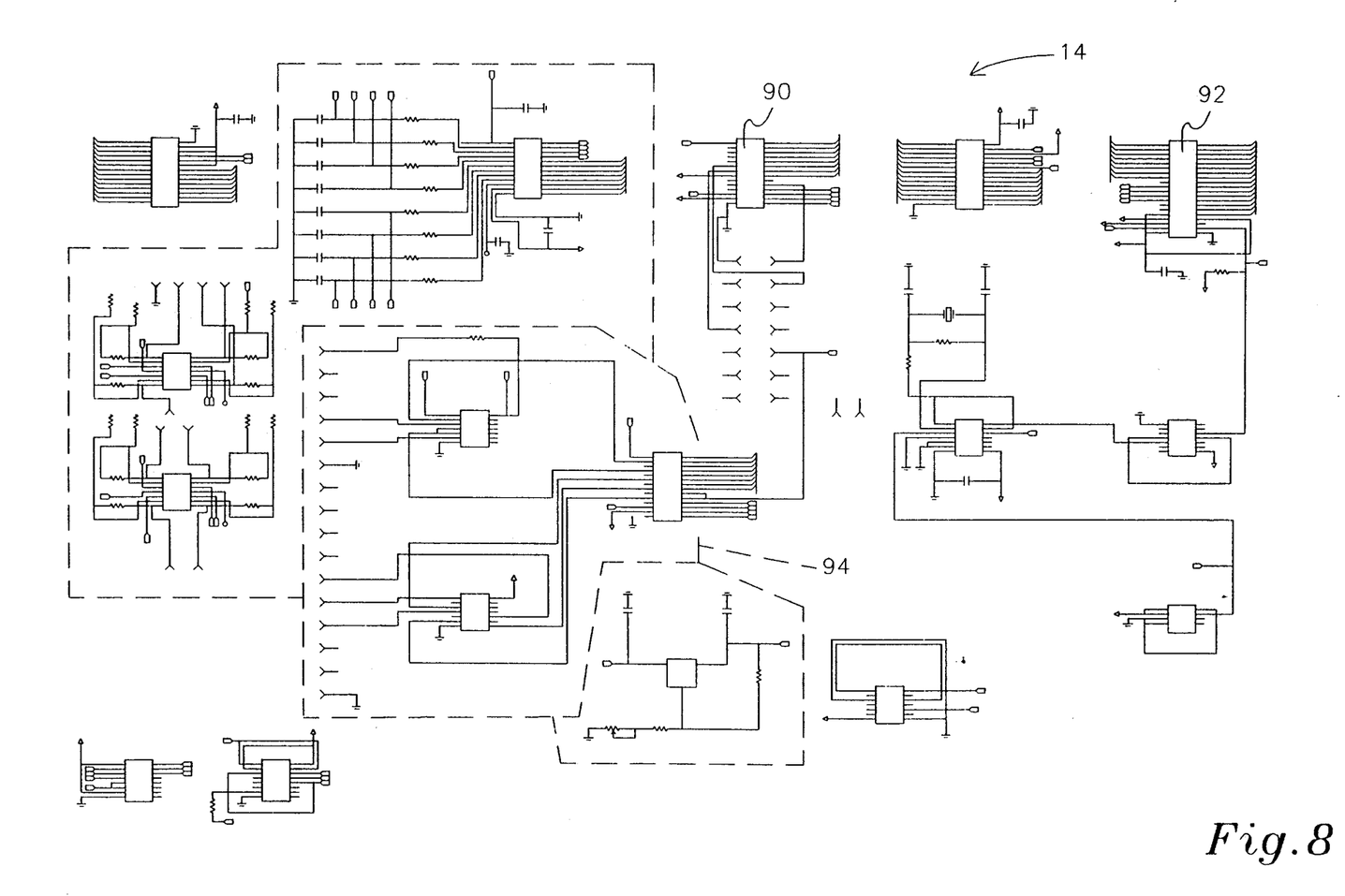
FIG. 8 is a schematic diagram of the circuitry of the input/output board incorporated in the receiver of FIG. 1.

The incoming data is processed by a selected microprocessor 92 such as the Zilog Z80. The microprocessor 92 inspects the checksum generated by the transmitter microcontroller 38. In the preferred embodiment, if any checksum is detected to be incorrect, the microprocessor 92 changes each number in the associated data set to zero as an indication to the system operator that the data is invalid. It will be understood that other forms of indication may be incorporated as well.

The data, whether found to be valid or invalid, is sent by the microprocessor 92 to a second communications interface 94. The second communications interface 94 of the preferred embodiment is configured to perform as a standard asynchronous serial port which may be connected to any standard computer serial port. The data may then be displayed and recorded as desired.

A selected software program has been developed to perform the selected functions of the improved EEG system 10. The software includes two segments, the first being an interrupt service routine, and the second being the main program.

The interrupt service program is normally initiated when the computer is booted, but may be initiated at any time prior to the initiation of the main program. The interrupt service program is executed one time, during which are performed initialization tasks such as reserving a selected amount of memory at a selected address. The interrupt service routine is a terminate and stay program which receives the decoded data from the FSK receiver 82 via a selected link. One selected link is a 19,200 baud RS-232 link. When a byte of data is received, the computer is interrupted and the data placed into a circular buffer in memory. The circular buffer of one embodiment is defined with a capacity of 16,000 (16 K) bytes of memory. This memory is located at a selected address in memory for accessibility by the main program.

The main program may be in the format of a Disk Operating System (DOS) program. The main program functions to retrieve data from the interrupt service routine circular buffer and format, display, and log the data to a series of disk files. From these disk files, previously recorded monitoring sessions may be reviewed, displayed, and/or printed at any selected time.

After initialization of the main program, the user will have the option to record a new session or to review a previously recorded session. If a new session is selected, the user will be requested to provide information about the subject. This information may include identification information regarding the patient and any comments an observer may wish to make. After response has been made to any initialization questions, the recording session will begin.

While the program is in the recording mode, each of the EEG signals is displayed as a single horizontal line of data. In the preferred embodiment, eight channels will produce eight horizontal lines of data to represent eight signals. The main program is designed such that each line of data scrolls from right to left on the display terminal such that the display contains the previous eight to ten seconds of data for each of the EEG signals received. Of course, the time of display for a single point of data is dependent on at least the rate of scroll and the dimensions of the display terminal. During the display of the data, recordation of the data is simultaneously being accomplished for later analysis, review and/or printing.

During the recordation of the monitoring session, several selected functions may be available to the user. Of these include: the selective viewing of vertical lines on the screen to indicate time increments such as 1-second intervals; the ability to freeze the display; the ability to change the vertical scale or sensitivity of the display; and the ability to make notations in the data file to emulate a clinician making notes on a paper polygraph. When selectively changing the appearance of the data on the screen—i.e., changing the scale, freezing the screen, etc.—the data being stored is unaltered. Therefore, a later review of the session will not reveal that these functions were utilized in the original session. When no data is being received by the software, the display terminal will cease to scroll.

When reviewing a previously recorded session, the user may scroll through the data in either forward or backward directions, vary the vertical scale as before, and add or remove the time increment indicators. Additionally, the user may print the screen being viewed, or he may print the entire data file as a continuous "tape" on a standard continuous form printer. Due to the digital transmission techniques as described above, the recordation of the data is ensured to be accurate such that the subsequent review of the data will be substantially identical to the viewing of the original session and no degradation of the data will occur.

From the foregoing description, it will be recognized by those skilled in the art that an EEG system 10 offering advantages over the prior art has been provided. Specifically, the EEG system 10 provides a means for adapting digital data communications techniques to the requirements of EEG recording. The EEG system 10 of the preferred embodiment includes a means for transmitting brain signals to a processing console for observation and recording. The data transmitted is selectively coded for accurate transmission. Means for verifying the accuracy of the transmitted data are provided, thereby allowing for the disposal of data which is distorted during transmission. Thus substantially all data observed and recorded is verified as accurate.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention.

1. An improved electroencephalograph system for telemetrically transmitting data to a selected receiver, said data being detected by a plurality of sensors selectively attached to a subject in a selected arrangement, said improved electroencephalograph system comprising:
   a first receiving means for receiving said data detected by said plurality of sensors, said data including signals indicating brain activity of said subject and used for selective monitoring of said subject;
   processing means for converting said data into a selected digital code suitable for telemetric transmission, said selected digital code being Manchester code;
   transmitting means for transmitting said coded data to said selected receiver at a selected frequency;
   second receiving means carried by said selected receiver to receive said coded data transmitted by said transmitting means;
   decoding means in communication with said second receiving means for decoding said coded data transmitted by said transmitting means; and
   user interface means for performing selected functions using said decoded data for continuous display/recording thereof.

2. The improved electroencephalograph system of claim 1 further comprising an amplification means for amplifying said data detected by said plurality of sensors and sending said amplified signals to said processing means.

3. The improved electroencephalograph system of claim 1 further comprising a data testing means for testing an integrity of said decoded data and further for indicating any of said data wherein said integrity has been damaged.

4. The improved electroencephalograph system of claim 3 wherein said data testing means includes a generator means, a comparator means and an identification means, said generator means for generating a selected indicator for simultaneous processing and transmission with said data detected by said plurality of sensors, said comparator means for comparing said selected indicator generated by said generator means with said selected indicator received after being coded by said processing means, transmitted by said transmitting means, and decoded by said decoding means, said identification means for identifying said decoded data transmitted simultaneously with said selected indicator when said decoded selected indicator varies from said selected indicator generated by said generator means.

5. The improved electroencephalograph system of claim 1 wherein said first receiving means includes a selected montage board for attaching said plurality of sensors in said selected arrangement.

6. The improved electroencephalograph system of claim 5 wherein said montage board is selectively removable for replacement by another said selected montage board defining another said selected arrangement.

7. The improved electroencephalograph system of claim 1 further comprising a frequency selecting means for selecting said selected frequency.

8. The improved electroencephalograph system of claim 1 wherein said user interface means is further used to perform at least a portion of said selected functions using said decoded data which has been previously recorded by said user interface means for continuous display thereof.

9. An improved electroencephalograph system for telemetrically transmitting data to a selected receiver, said data being detected by a plurality of sensors selectively attached to a subject in a selected arrangement, said improved electroencephalograph system comprising:
   a first receiving means for receiving said data detected by said plurality of sensors, said first receiving means including a selected montage board for attaching said plurality of sensors in said selected arrangement, said data including signals indicating brain activity of said subject and used for selective monitoring of said subject;
   amplification means for amplifying said data;
   processing means for converting said amplified data into a selected digital code suitable for telemetric transmission, said processing means including a generator means for generating a selected indicator for simultaneous processing and transmission with said amplified data, said selected digital code being Manchester code;
   transmitting means for transmitting said coded data and said coded indicator to said selected receiver at a selected frequency;
   second receiving means carried by said selected receiver to receive said coded data and said coded indicator transmitted by said transmitting means;
   decoding means in communication with said second receiving means for decoding said coded data and said coded indicator transmitted by said transmitting means;
   comparator means for comparing said selected indicator generated by said generator means with said decoded indicator received after being decoded by said decoding means;
   identification means for identifying said decoded data transmitted simultaneously with said selected indicator when said decoded indicator varies from said selected indicator generated by said generator means; and
   user interface means for performing selected functions using said decoded data for continuous display/recording thereof and further to perform at least a portion of said selected functions using said decoded data which has been previously recorded by said user interface means for continuous display thereof.

10. The improved electroencephalograph system of claim 9 wherein said montage board is selectively removable for replacement by another said selected montage board defining another said selected arrangement.

11. The improved electroencephalograph system of claim 9 further comprising a frequency selecting means for selecting said selected frequency.

12. A method of telemetrically transmitting signals sensed using an improved electroencephalograph system for transmitting data to a selected receiver, said method of telemetrically transmitting signals comprising the steps of:

sensing said signals by a plurality of sensors selectively attached to a subject in a selected arrangement;

sending said signals to a selected processing means;

amplifying said signals within said processing means;

generating a selected indicator for simultaneous processing with said amplified signals;

converting said amplified signals and said selected indicator into a selected digital code suitable for telemetric transmission, said selected digital code being Manchester code;

transmitting said coded signals and said coded indicator at a selected frequency;

receiving said coded signals and said coded indicator by a selected receiving means;

decoding said coded signals and said coded indicator;

comparing said selected indicator with said decoded indicator;

identifying said decoded signals transmitted simultaneously with said decoded indicator when said decoded indicator varies from said selected indicator generated by said generator means; and selectively and continuously displaying and recording said decoded signals.

13. The method of telemetrically transmitting signals of claim 12 further comprising the step of selecting said arrangement for said attachment of said plurality of sensors to said subject prior to said step of sensing said signals by said plurality of sensors selectively attached to said subject in said selected arrangement.

14. The method of telemetrically transmitting signals of claim 12 further comprising the step of selecting said frequency prior to said step of transmitting said coded signals and said coded indicator at said selected frequency.

* * * * *